United States Patent
Spear et al.

(10) Patent No.: US 8,855,765 B2
(45) Date of Patent: Oct. 7, 2014

(54) FAULT TOLERANT METHODS AND ARCHITECTURES FOR EMBEDDED INTELLIGENCE IN MEDICAL LEADS

(75) Inventors: Thomas H. Spear, Bloomington, MN (US); Nancy M. Germanson, Maple Grove, MN (US); Patrick D. Miller, Circle Pines, MN (US)

(73) Assignee: Medtronic, Inc., Minneapolis, MN (US)

( * ) Notice: Subject to any disclaimer, the term of this patent is extended or adjusted under 35 U.S.C. 154(b) by 519 days.

(21) Appl. No.: 13/156,632

(22) Filed: Jun. 9, 2011

(65) Prior Publication Data

US 2012/0316416 A1  Dec. 13, 2012

(51) Int. Cl.
- *A61N 1/08* (2006.01)
- *A61N 1/05* (2006.01)
- *A61N 1/04* (2006.01)
- *A61B 5/0402* (2006.01)
- *A61B 5/00* (2006.01)

(52) U.S. Cl.
CPC .............. *A61N 1/056* (2013.01); *A61N 1/0488* (2013.01); *A61B 5/0402* (2013.01); *A61B 5/7217* (2013.01); *A61N 1/08* (2013.01); *A61N 2001/083* (2013.01)
USPC ................................ 607/28; 607/27; 600/508

(58) Field of Classification Search
CPC ....... A61N 1/0488; A61N 1/056; A61N 1/08; A61B 5/0402
USPC ................................ 607/27, 28, 119; 600/508
See application file for complete search history.

(56) References Cited

U.S. PATENT DOCUMENTS

| | | |
|---|---|---|
| 3,888,261 A | 6/1975 | Maurer |
| 4,105,900 A | 8/1978 | Martin et al. |
| 4,140,131 A | 2/1979 | Dutcher et al. |
| 4,549,548 A | 10/1985 | Wittkampf et al. |
| 4,579,119 A | 4/1986 | Callaghan |
| 4,606,349 A | 8/1986 | Livingston et al. |
| 4,620,303 A | 10/1986 | Tschoepe |
| 4,899,750 A | 2/1990 | Ekwall |

(Continued)

FOREIGN PATENT DOCUMENTS

| | | |
|---|---|---|
| EP | 0715866 A2 | 6/1996 |
| WO | 98/42406 A1 | 10/1998 |

(Continued)

OTHER PUBLICATIONS

Case Report, "Early Detection of Lead Fracture by Painless High Voltage Lead Impedance Measurement in a Transvenous ICD Lead System", by Jens Stevens MD., et al., Journal of Interventional Cardiac Electrophysiology 4, 269-272 (2000).

(Continued)

*Primary Examiner* — Tammie K Heller
(74) *Attorney, Agent, or Firm* — Evans M. Mburu (57) ABSTRACT

The present disclosure pertains to methods, devices and systems for detection of a lead-related condition in a medical electrical lead. In accordance with the disclosure, a physiological waveform interpreter module embedded within the lead functions to sense the occurrence of a cardiac event and to generate a minimal impact signal. In an example implementation, the physiological waveform interpreter module is disposed proximate to the sensing site or vicinity of cardiac signals. The physiological waveform interpreter module transmits the minimal impact signal that may include one or more predetermined properties to a remotely located lead monitoring module upon sensing a cardiac event. The lead monitoring module receives and processes the minimal impact signal to determine whether a cardiac depolarization has occurred and simultaneously verify the integrity of the transmission medium.

18 Claims, 7 Drawing Sheets

(56) References Cited

U.S. PATENT DOCUMENTS

| | | | |
|---|---|---|---|
| 4,916,612 | A | 4/1990 | Chin et al. |
| 5,003,975 | A | 4/1991 | Hafelfinger et al. |
| 5,117,824 | A | 6/1992 | Keimel et al. |
| 5,137,021 | A | 8/1992 | Wayne et al. |
| 5,156,149 | A | 10/1992 | Hudrlik |
| 5,184,614 | A | 2/1993 | Collins et al. |
| 5,201,808 | A | 4/1993 | Steinhaus et al. |
| 5,201,865 | A | 4/1993 | Kuehn |
| 5,224,475 | A | 7/1993 | Berg et al. |
| 5,344,430 | A | 9/1994 | Berg et al. |
| 5,350,410 | A | 9/1994 | Kleks et al. |
| 5,361,776 | A | 11/1994 | Samuelson et al. |
| 5,402,070 | A | 3/1995 | Shelton et al. |
| 5,431,692 | A | 7/1995 | Hansen et al. |
| 5,453,468 | A | 9/1995 | Mascia et al. |
| 5,476,485 | A | 12/1995 | Weinberg et al. |
| 5,507,786 | A | 4/1996 | Morgan et al. |
| 5,534,018 | A | 7/1996 | Wahlstrand et al. |
| 5,549,646 | A | 8/1996 | Katz et al. |
| 5,722,997 | A | 3/1998 | Nedungadi et al. |
| 5,741,311 | A | 4/1998 | Mc Venes et al. |
| 5,755,742 | A | 5/1998 | Schuelke et al. |
| 5,765,031 | A | 6/1998 | Mimuth et al. |
| 5,814,088 | A | 9/1998 | Paul et al. |
| 5,891,179 | A | 4/1999 | Er et al. |
| 5,944,746 | A | 8/1999 | Kroll |
| 6,052,753 | A | 4/2000 | Doerenberg et al. |
| 6,445,951 | B1 | 9/2002 | Mouchawar |
| 6,493,586 | B1 | 12/2002 | Stahmann et al. |
| 6,721,600 | B2 | 4/2004 | Jorgenson et al. |
| 6,859,667 | B2 | 2/2005 | Goode |
| 6,871,091 | B2 | 3/2005 | Wilkinson et al. |
| 7,047,083 | B2 | 5/2006 | Gunderson et al. |
| 7,149,580 | B2 | 12/2006 | Conley et al. |
| 7,225,025 | B2 | 5/2007 | Goode |
| 7,236,834 | B2 | 6/2007 | Christopherson et al. |
| 7,389,144 | B1 | 6/2008 | Osorio et al. |
| 7,515,961 | B2 | 4/2009 | Germanson et al. |
| 2002/0120307 | A1 | 8/2002 | Jorgenson et al. |
| 2003/0204233 | A1 | 10/2003 | Laske et al. |
| 2005/0043768 | A1 | 2/2005 | Goode |
| 2005/0090870 | A1 | 4/2005 | Hine et al. |
| 2006/0064149 | A1 | 3/2006 | Belacazar et al. |
| 2007/0265674 | A1 | 11/2007 | Olson et al. |
| 2010/0027176 | A1 | 2/2010 | Kawate et al. |
| 2010/0063561 | A1 | 3/2010 | Sloman et al. |
| 2010/0106206 | A1 | 4/2010 | Aghassian et al. |
| 2010/0114222 | A1 | 5/2010 | Gunderson et al. |
| 2010/0217366 | A1 | 8/2010 | Moulder et al. |
| 2010/0324640 | A1 | 12/2010 | Bauer et al. |
| 2011/0054554 | A1 | 3/2011 | Swerdlow |

FOREIGN PATENT DOCUMENTS

| | | |
|---|---|---|
| WO | 2009082783 | 7/2009 |
| WO | 2010/008833 A1 | 1/2010 |
| WO | 2010056501 A1 | 5/2010 |

OTHER PUBLICATIONS

NASA Office of Logic Design, "Fault Tolerant Design", Preferred Reliability Practices No. PD-ED-1246, Sep. 21, 1995, pp. 1-4.

Avizienis et al., "Basic Concepts and Taxonomy of Dependable and Secure Computing", IEEE Transactions on Dependable and Secure Computing, vol. 1, No. 1, Jan.-Mar. 2004, pp. 11-33.

Avizienis, "Toward Systematic Design of Fault-Tolerant Systems", IEEE, Apr. 1997, pp. 51-58.

Dorwarth et al., "Transvenous Defibrillation Leads: High Incidence of Failure During Long-Term Follow-Up", J. Cardiovascular Electrophysiol., vol. 14, Jan. 2003, pp. 38-43.

(PCT/US2012/040666) PCT Notification of Transmittal of the International Search Report and the Written Opinion of the International Searching Authority, Mailed Aug. 10, 2012, 10 pages.

FAULT TOLERANT METHODS AND ARCHITECTURES FOR EMBEDDED INTELLIGENCE IN MEDICAL LEADS

CROSS-REFERENCE TO RELATED APPLICATIONS

This patent application is related to the commonly-assigned related U.S. patent application Ser. No. 13/014,965 entitled "ISOLATING LEAD CONDUCTOR FOR FAULT DETECTION" and U.S. patent application Ser. No. 13/015,042, entitled "ISOLATED LEAD CONDUCTOR MEASUREMENTS FOR FAULT DETECTION" both filed on Jan. 27, 2011 and both of which are incorporated herein by reference in their entirety. The application is also related to U.S. patent application Ser. No. 13/156,660, filed concurrently herewith entitled "METHOD AND APPARATUS TO MANAGE LEAD-RELATED CONDITIONS FOR FAULT TOLERANCE ENHANCEMENTS" which is incorporated herein by reference in its entirety.

TECHNICAL FIELD

The present disclosure generally relates to implantable medical devices including stimulation therapies and/or sensing. More particularly, various exemplary mechanisms of the disclosure concern implantable medical device diagnostics such as the condition of medical electrical lead systems used for pacing, shock, detection, sensing and/or stimulation.

BACKGROUND

The human anatomy includes many types of tissues that can either voluntarily or involuntarily, perform certain functions. After disease, injury, or natural defects, certain tissues may no longer operate within general anatomical norms. For example, organs such as the heart may begin to experience certain failures or deficiencies. Some of these failures or deficiencies can be diagnosed, corrected or treated with implantable medical devices (IMDs), such as heart monitors, pacemakers, implantable cardioverter-defibrillators (ICDs), myostimulators, nerve stimulators, drug delivery devices, subcutaneous defibrillators, and several other known IMDs.

IMDs for monitoring a physiological condition or delivering a therapy typically rely on one or more sensing element such as sensors and/or electrodes positioned in a patient's blood vessel, heart chamber, or other portion of the body. Raw signals relating to a physiological condition from which a patient condition or the need for therapy can be assessed are generally sensed by the sensing element. The raw signals are typically transmitted to the IMD for processing through implantable medical electrical lead(s) associated with the sensing element. In other types of IMDs or implantable systems, additional leads may be used for applying a therapy stimulus to various body areas such as the spinal column. These leads typically include a lead body extending between a proximal lead end and a distal lead end and the sensing element is typically incorporated on or along the length of the lead such as near the distal end.

Implantable medical leads can extend from a subcutaneous implantation site of the IMD through an internal body pathway to a desired tissue site. The leads are generally preferred having small diameter, highly flexible, lead bodies that withstand degradation by body fluids and body movements that apply chemical or physical stress and strain to the lead body and the connections made to sensing element. As lead bodies are made smaller and smaller and the number of lead conductors is increased or maintained, the integrity of lead conductors and insulators is increasingly important.

Various studies indicate that an implanted lead may degrade for one or more reasons. For example, a study by Dorwarth et al., "Transvenous defibrillation leads: high incidence of failure during long-term follow-up," J Cardiovasc Electrophysiol., 14(1):38-43 (2003), found that a majority of lead-related sensing failures were associated with insulation defects that occurred late after ICD placement (6.0+/−1.8 years after implant). Dorwarth et al. observed that "automated device control features with patient alert function integrated into new devices may contribute to early detection of lead failure."

As described herein, the present disclosure addresses the need in the art for mechanisms that support early detection of a lead-related condition and or graceful degradation in the emergence of a lead-related condition.

SUMMARY

Implantable cardiac systems are used to sense electrical activity indicating an intrinsic contraction of the heart chamber of a patient. In particular, an electrical lead and electrode(s) are placed in or proximate to the heart and signals indicative of the electrical activity are transmitted through the lead to an implantable medical device (IMD) for processing. The presence or absence of the sensed contraction and the timing of the sensed contractions, are used to control the cardiac pacing system for the patient's well being. In conventional systems, the sensed electrical signals are transmitted in a raw form through the lead for processing by the IMD. One aspect of such systems is the difficulty of determining when the physiological signal is distorted or corrupted by external sources, such as electromagnetic influence, and system hardware induced behaviors such as conductor noise and/or other undesirable electrical properties.

In general and as will further be described in exemplary embodiments, the present disclosure describes methods, devices and systems that include a physiological waveform interpreter (PWI) function localized within a lead at the site or vicinity of a signal source. The PWI function transmits a minimal impact signal to a lead monitoring function that receives and processes the minimal impact signal to determine the integrity of the transmission medium and/or the occurrence of a cardiac event.

In accordance with the foregoing, one embodiment includes an electronic assembly for an implantable medical device. The electronic assembly includes a PWI module in electrical communication with a device monitoring and processing module. In examples, the electronic assembly receives cardiac electrical signals and detects a cardiac event. In response to detecting the cardiac event, the PWI will generate a minimal impact signal having a predetermined set of signal properties. The device monitoring module receives the minimal impact signal and processes the received signal to determine whether the received signal matches or is confirmed by the transmitted PWI signal. In some embodiments, the device monitoring module may be remotely located and coupled by the transmission medium to the PWI module.

In another embodiment, an implantable medical lead assembly is provided including an electronic assembly disposed within the medical lead body. The electronic assembly includes a PWI module coupled to one or more sensing elements such as an electrode or physiological sensor associated with the medical lead and a lead monitoring module electrically coupled to the PWI module. The electrical coupling of the PWI module and the lead monitoring module may be through a conductor or other waveguide. In an embodiment, the PWI module is disposed at a distal portion of the lead and the lead monitoring module is disposed adjacent to a proximal portion of the lead. The electronic assembly comprises an electronic network for receiving signals sensed by the electrodes, detecting a cardiac event, generating and transmitting a PWI signal and determining the integrity of the transmitted signal.

In yet another embodiment, an implantable medical system is provided having a medical device coupled to an implantable medical lead assembly. The implantable medical lead assembly includes an electronic assembly comprising a PWI module in electrical communication with a lead monitoring module. The PWI module transmits a first signal to the lead monitoring module and the lead monitoring module monitors a transmission medium coupling the modules to determine whether the transmitted signal is received. In examples, the lead monitoring module performs signal comparison to determine whether a received signal matches or confirms the pattern of the first signal in response to receiving the signal. In one embodiment, a second signal may be generated by the lead monitoring module based on the results of the signal comparison. In one implementation, the medical device comprises a processing module for receiving the second signal and determining an action to be taken. For example, a lead-related condition is declared in response to the second signal denoting a mismatch or lack of conformation between the received signal and the transmitted first signal.

In another example, the result of the signal comparison triggers the declaration of a lead-related condition and the second signal is generated as an alert to notify a user of the lead-related condition. In yet another example, the result of the signal comparison triggers the declaration of a lead-related condition and the second signal serves as an interrupt for the device operations, including the pace and sense functions.

BRIEF DESCRIPTION OF THE DRAWINGS

The following drawings are illustrative of particular embodiments of the present disclosure and therefore do not limit the scope of the disclosure. The drawings (not to scale) are intended for use in conjunction with the explanations in the following detailed description, wherein similar elements are designated by identical reference numerals. Moreover, the specific location of the various features is merely exemplary unless noted otherwise.

DETAILED DESCRIPTION

The following detailed description is merely exemplary in nature and is not intended to limit the disclosure or the application and uses of the disclosure. Furthermore, there is no intention to be bound by any expressed or implied theory presented in the preceding technical field, background, brief summary or the following detailed description.

For convenience, unless otherwise indicated the term "IMD" is inclusive of any implantable medical device capable of administering any of a number of therapies to the heart or other organs or other tissue of the patient. Illustrative embodiments of the present disclosure have been presented in the context of a cardiac pacemaker, it being understood that the disclosure certainly has applicability to many other types of IMDs. For example, while the present disclosure will be described with reference to the use of medical electrical leads having electrodes that monitor or treat a heart, it will be appreciated that the present disclosure may be used in conjunction with any suitable medical lead having a sensor, stimulator or other treatment device adapted for a sensing and/or therapy application. It is believed that description of all types of such sensors, stimulators and treatment devices is not necessary and reference is therefore only made to electrode-carrying leads. In addition, the diagnostics functions attributable to an IMD may similarly be performed by an analyzer that is typically coupled to the lead during implant or device change-out for various diagnostics purposes.

Figure 1:
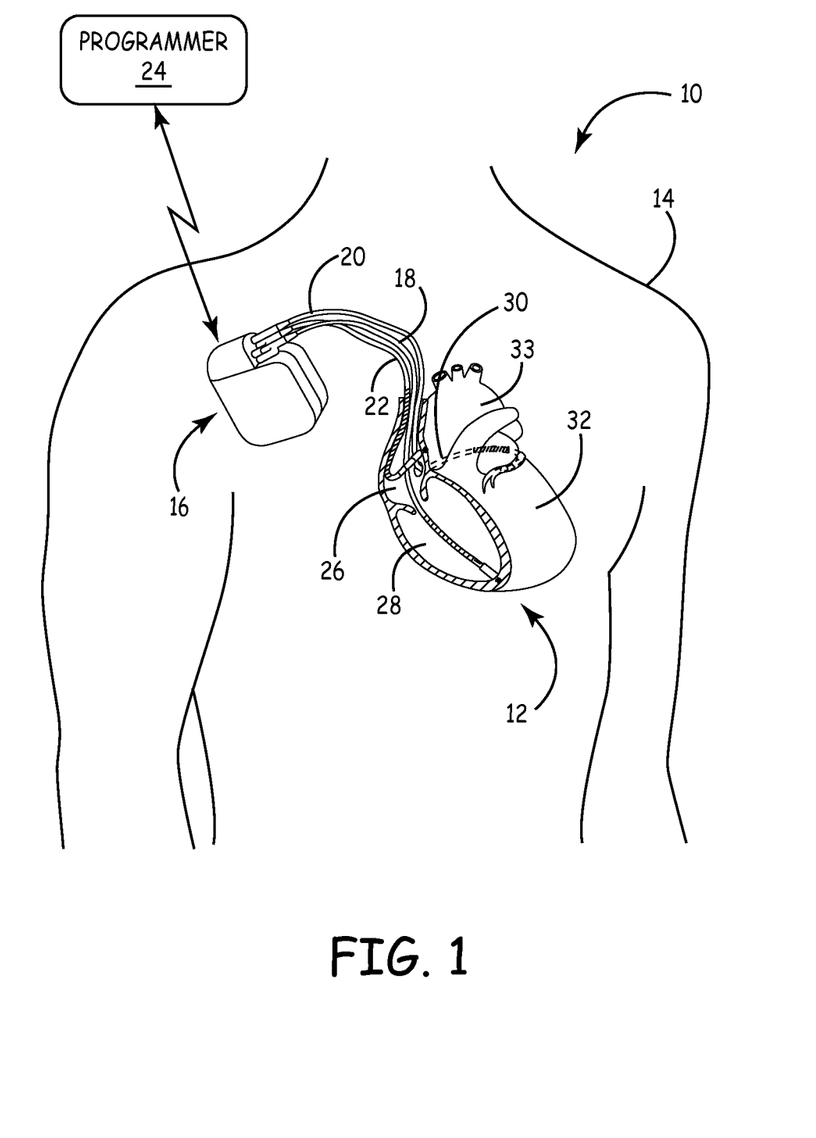
FIG. 1 is a conceptual diagram illustrating an example therapy system that may be used to provide therapy to a heart of a patient.

FIG. 1 is a conceptual diagram illustrating an example therapy system 10 that may be used to provide therapy to heart 12 of patient 14. Patient 14 ordinarily, but not necessarily, will be a human. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Each of leads 18, 20 and 22 may carry one or a set of electrodes. The electrode may extend about the circumference of each of leads 18, 20, and 22 and is positioned at a respective axial position along the length of each of the lead 18, 20, and 22.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. In alternative embodiments, the LV lead 20 may also be introduced into the left ventricle through the septal wall. Right atrial (RA) lead 22 extends through one or more veins and the vena cava, and into the right atrium 26 of heart 12.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may also provide defibrillation therapy and/or cardioversion therapy via electrodes located on at least one of the leads 18, 20, 22. IMD 16 may detect arrhythmia of heart 12, such as fibrillation of ventricles 28 and 32, and deliver defibrillation therapy to heart 12 in the form of electrical pulses. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art.

In some examples, programmer 24 may be a handheld computing device or a computer workstation. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display.

A user, such as a patient, physician, technician, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or tachyarrhythmia episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20, and 22, or a power source of IMD 16.

The user may use programmer 24 to program a therapy progression, select electrodes used to deliver defibrillation shocks, select waveforms for the defibrillation shock, or select or configure a fibrillation detection algorithm for IMD 16. The user may also use programmer 24 to program aspects of other therapies provided by IMD 16, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
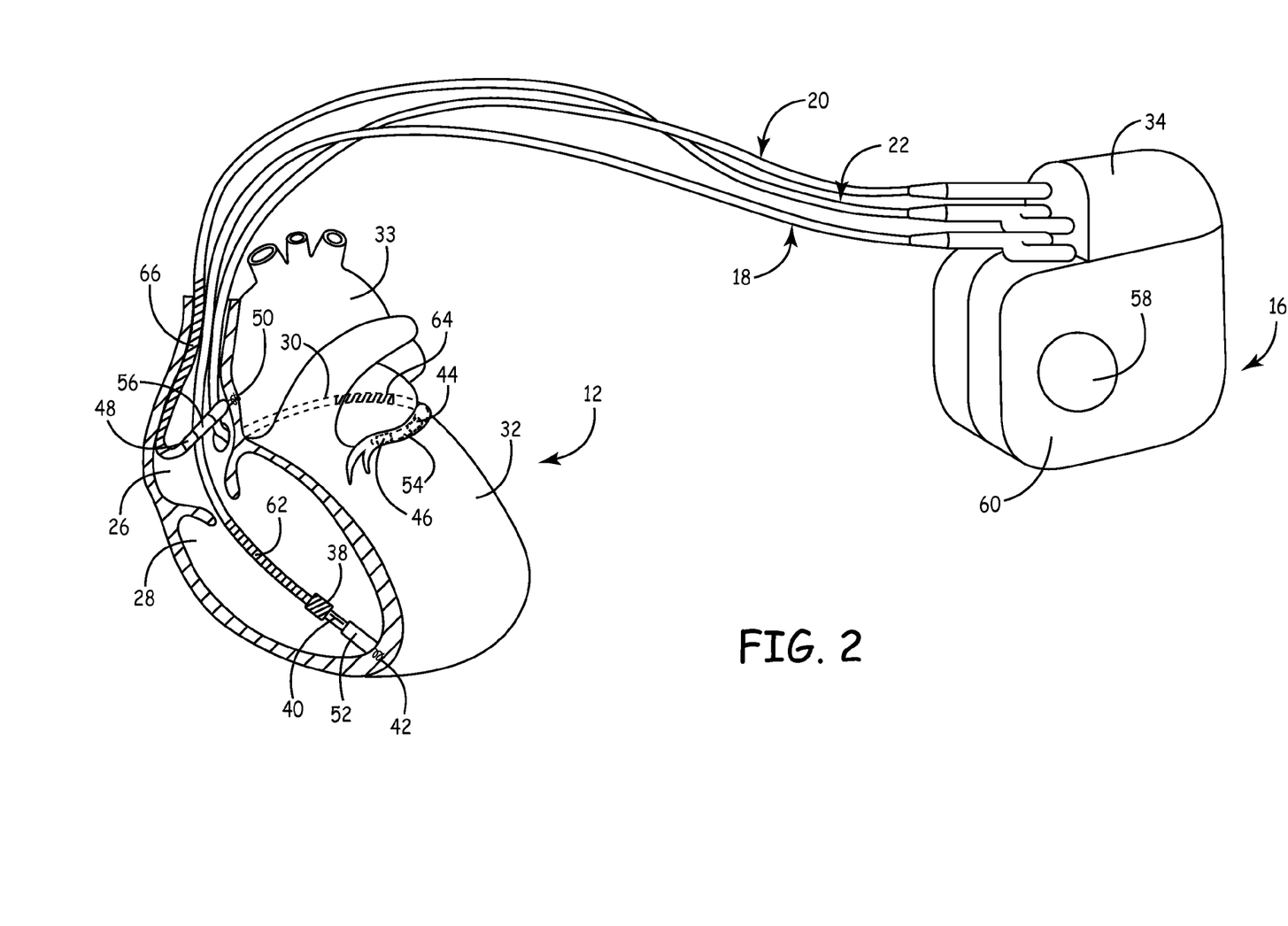
FIG. 2 is a conceptual diagram illustrating an implantable medical device and leads of therapy system in greater detail.

FIG. 2 is a conceptual diagram illustrating IMD 16 and leads 18, 20, 22 of therapy system 10 in greater detail. Leads 18, 20, 22 may be electrically coupled to a stimulation generator, a sensing module, or other modules of IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors, or parallel cable conductors in a multi-lumen lead body or co-radial conductors all of which are separated from one another by tubular insulative sheaths. In the illustrated example, a pressure sensor 38 and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22. In FIG. 2, pressure sensor 38 is disposed in right ventricle 28. Pressure sensor 30 may respond to an absolute pressure inside right ventricle 28, and may be, for example, a capacitive or piezoelectric absolute pressure sensor. In other examples, pressure sensor 30 may be positioned within other regions of heart 12 and may monitor pressure within one or more of the other regions of heart 12, or may be positioned elsewhere within or proximate to the cardiovascular system of patient 14 to monitor cardiovascular pressure associated with mechanical contraction of the heart.

Among the electrodes, some of the electrodes may be provided in the form of coiled electrodes that form a helix, while other electrodes may be provided in different forms. Further, some of the electrodes may be provided in the form of tubular electrode sub-assemblies that can be pre-fabricated and positioned over the body of leads 18, 20, 22, where they are attached and where electrical connections with conductive elements within the leads 18, 20, 22 can be made. For example, electrodes 40, 44 and 48 may take the form of ring electrodes, and electrodes 42, 46 and 50 may take the form of extendable helix tip electrodes mounted retractably within insulative electrode heads 52, 54 and 56, respectively. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. In some examples, IMD 16 also delivers pacing pulses via electrodes 40, 42, 44, 46, 48 and 50 to cause depolarization of cardiac tissue of heart 12. In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define one or more housing electrodes. In some examples, housing electrode 58 comprises substantially all of housing 60. Any of the electrodes 40, 42, 44, 46, 48 and 50 may be used for unipolar sensing or pacing in combination with housing electrode 58. As is known in the art, housing 60 may enclose a stimulation generator that generates cardiac pacing pulses and defibrillation or cardioversion shocks, as well as a sensing module for monitoring the patient's heart rhythm.

Leads 18, 20, 22 also include elongated electrodes 62, 64, 66, respectively, which may take the form of a coil. IMD 16 may deliver defibrillation shocks to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in constructing implantable electrodes including various surface treatment materials and processes.

Pressure sensor 38 may be coupled to one or more coiled conductors within lead 18. In FIG. 2, pressure sensor 38 is located more distally on lead 18 than elongated electrode 62. In other examples, pressure sensor 38 may be positioned more proximally than elongated electrode 62, rather than distal to electrode 62. Further, pressure sensor 38 may be coupled to another one of the leads 20, 22 in other examples, or to a lead other than leads 18, 20, 22 carrying stimulation and sense electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation shocks and other therapies to heart 12 via percutaneous leads that extend through the skin of patient 14 to a variety of positions within or outside of heart 12.

In other examples of therapy systems that provide electrical stimulation therapy to heart 12, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 33. Other examples of therapy systems may include a single lead that extends from IMD 16 into right atrium 26 or right ventricle 28, or two leads that extend into a respective one of the right ventricle 26 and right atrium 28. An example of this type of therapy system is shown in FIG. 3.

Figure 3:
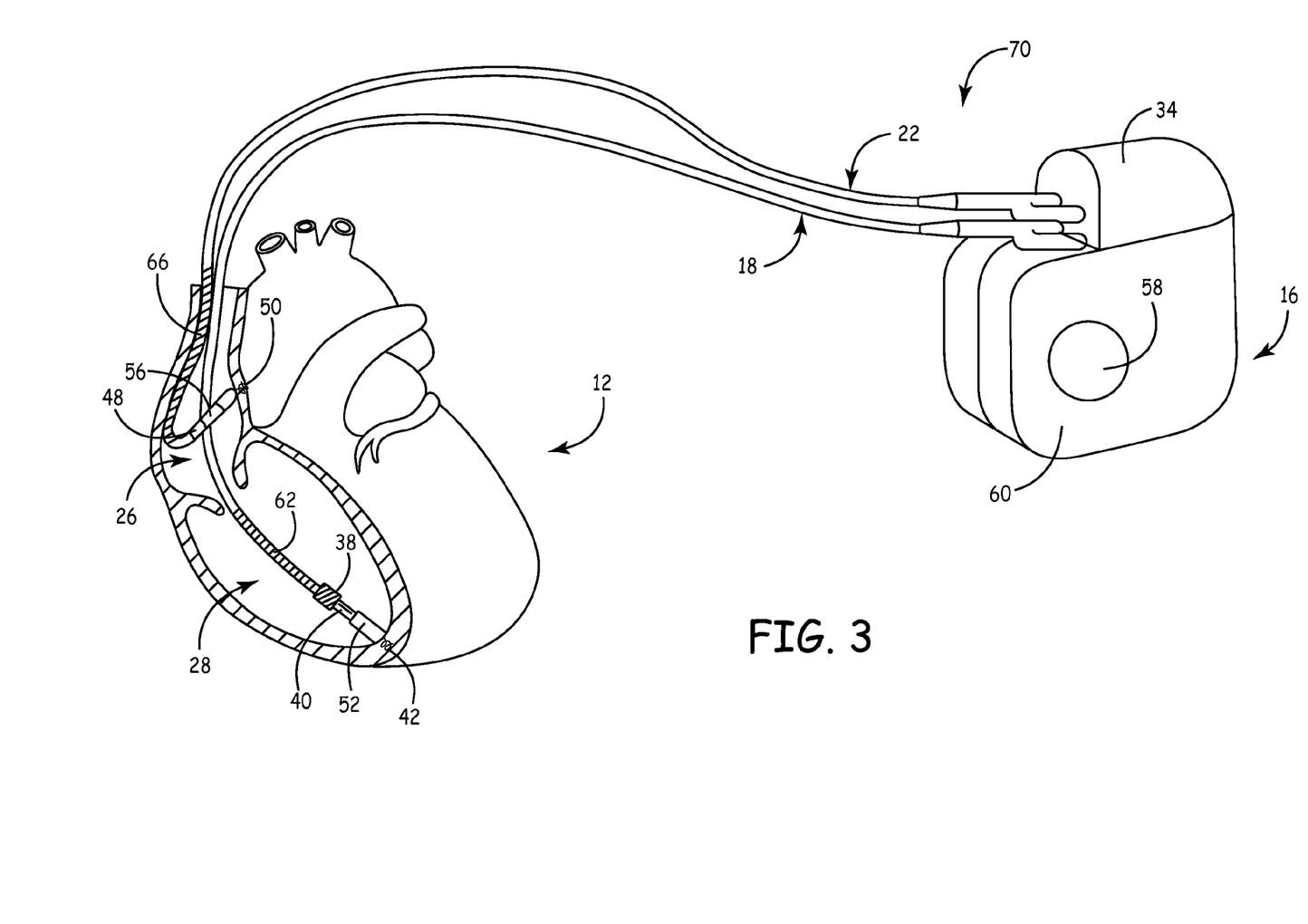
FIG. 3 is a conceptual diagram illustrating another exemplary therapy system.

FIG. 3 is a conceptual diagram illustrating another example of therapy system 70, which is similar to therapy system 10 of FIGS. 1-2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12.

In constructing the bodies of leads 18, 20, 22, various considerations are typically taken into account to maintain the integrity of the implanted leads. One such consideration is the continuous flexing of the leads 18, 20, 22 due to the beating of the heart. Other considerations are the stresses applied to the lead body during an implantation or lead repositioning procedure. Movements by the patient can cause the route traversed by the lead body to be constricted or otherwise altered causing stresses on the lead body. At times, the lead bodies can be slightly damaged because of improper handling during surgical implantation, and the slight damage can progress in the body environment until a lead conductor fractures and/or the insulation is breached. The effects of lead body degradation can progress from an intermittent manifestation to a more continuous effect and this may occur gradually over time or instantaneously. In extreme cases, insulation of one or more of the electrical conductors can be breached, causing the conductors to contact one another or body fluids resulting in a low impedance or short circuit. In other cases, a lead conductor can fracture and exhibit an intermittent or continuous open circuit resulting in intermittent or continuous high impedance as well as noise. These and other such lead issues affecting the conductive pathway, which is comprised of one or both the conductor and insulation, and resulting in partial or complete short or open circuits, for example, can be referred to, for simplicity, as "lead-related conditions."

In other words, a lead-related condition is any lead hardware degradation that has crossed a threshold that increases the probability of electrical characteristics or behaviors that could lead to a malfunction of an implantable medical system if the condition is persists. In the case of cardiac leads, the ability to sense cardiac activity conditions accurately through a lead can be impaired by these lead-related conditions. Complete lead breakage impedes any sensing functions while lead conductor fractures or intermittent contact can demonstrate electrical noise that interferes with accurate sensing. During cardiac pacing or defibrillation therapy, lead-related conditions can reduce the effectiveness of a pacing or defibrillation therapy below that sufficient to pace or defibrillate the heart. The lead-related conditions can also prevent the IMD from deciding to deliver the therapy when needed or can cause the IMD to deliver therapy when not needed.

As depicted in FIGS. 1-3, one or more of leads 18, 20, 22 are electrically coupled to medical device 16 that is implanted at a medically suitable location in patient 10 during use. The leads 18, 20, 22 extend from medical device 16, where the proximal ends are connected, to another suitable location in the patient where the distal end portions are adjacent to the desired organ/tissue of patient 10. For ease of description, the concepts pertaining to the present disclosure will be described in FIGS. 4-8 herein, in relation to lead 18—it being understood that the same applies to any of the other leads 20, 22.

Figure 4:
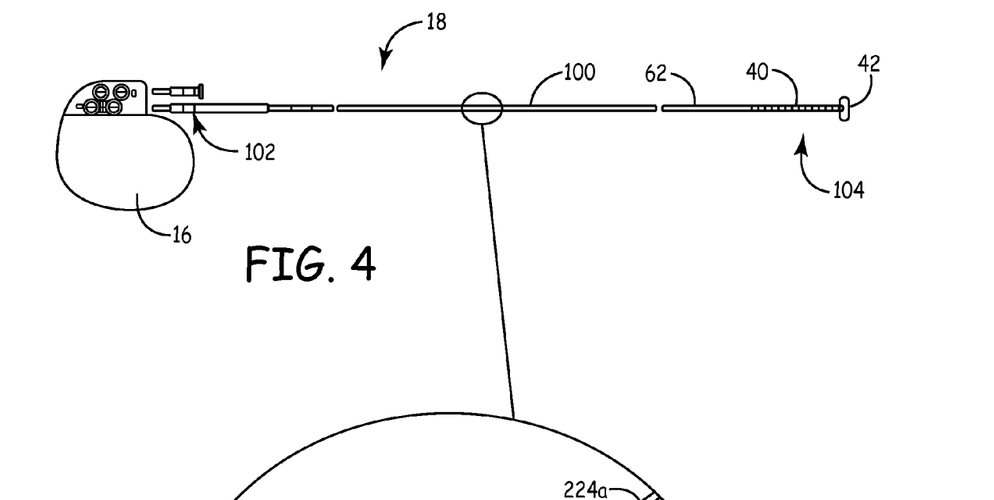
FIG. 4 is a plan view of an implantable medical device system including a medical electrical lead coupled to an implantable medical device according to an embodiment of the present disclosure.

With that in mind, FIG. 4 is a plan view of the medical electrical lead 18 including an active electronic circuit according to an embodiment of the present disclosure. FIG. 4 illustrates lead 18 including a lead body 100 having a proximal portion 102 and a distal portion 104. The electronic assembly 120 may be disposed within lead body 100. The electronic assembly 120 and its contents will be described in greater detail below. Alternatively, the lead body 100 houses an electronic assembly 120 that may be housed in an encasement 108. One exemplary encasement 108 for housing electronic assembly 120 is described in U.S. Pat. No. 7,236,834, issued to Christopherson et al., which is incorporated herein by reference in its entirety.

One or more conductors 224a electrically couple the electronic assembly 120 at a proximal end to the IMD 16. The distal end of the electronic assembly 120 is also coupled with the electrodes 62, 40, and 42 via a corresponding set of conductors 224b. Although the conductors 224a and 224b (collectively "224") are illustrated as being separate conductors, it should be appreciated that the conductors 224a and 224b may take the form of a unitary cable/wire. Conductors for coupling each electrode 62, 40, and 42 are typically electrically insulated and extend within lead body 100. Arrangements of the conductors within lead body 100 are known and include coaxial positioning, non-coaxial positioning and a combination thereof. According to one exemplary embodiment, lead body 100 is formed in part by a silicone or polyurethane multilumen tube, wherein each lumen carries one or more conductors. Optionally, a connector block 110 can be fastened to the encasement 108. The connector block 110 electrically connects one or more conductors 224 to the electronic assembly 120 via connectors such as lead clamps (not shown) that hold the conductors 224 in place using tightening set screws or any other known securing techniques.

The electronic assembly 120 includes circuitry and other components that may include stand-alone sensing and/or therapeutic devices that operate in an independent and self-contained manner. In an example, the electronic assembly 120 is in-line with the lead body 100 and consequently enables the electronic assembly 120 to be disposed anywhere within the lead body 100.

Figure 5:
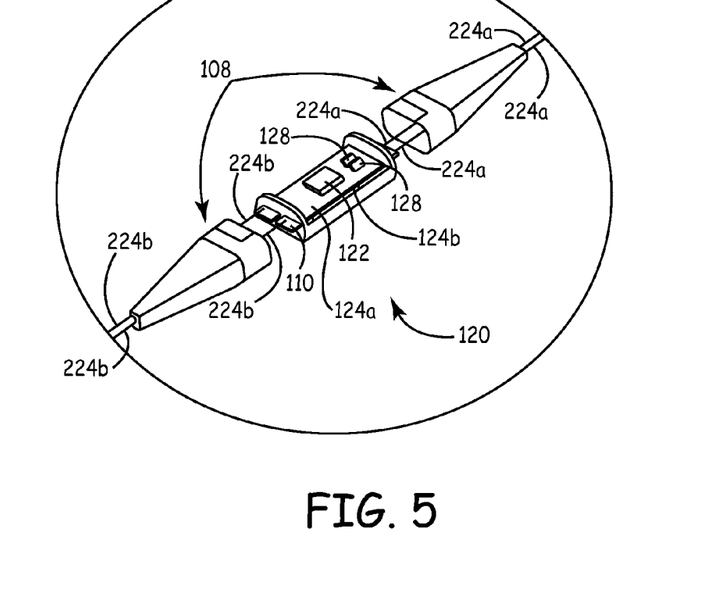
FIG. 5 illustrates a perspective view of one embodiment of an electronic assembly disposed within a medical electrical lead in accordance with the disclosure.

Turning next to FIG. 5, one embodiment of electronic assembly 120 is illustrated. The electronic assembly 120 includes an energy source 122 and integrated electrical circuitry/components such as a physiological waveform interpreter (PWI) module 124a and lead monitoring circuit 124b (collectively "integrated circuitry 124"). Energy source 122 may include a lithium rechargeable battery or an energy harvesting circuit. The electronic assembly 120 may be configured to integrate both monitoring and therapy features. For monitoring, electronic assembly 120 collects and processes data about heart 12 from one or more electrodes. Therapy may subsequently be provided by electronic assembly 120 based on the monitored data, as desired. As such, electronic assembly 120 includes various components as appropriate to produce the desired functionalities of the device.

In another embodiment, the electronic assembly 120 may be powered by dedicated conductive lines from the IMD. In yet another embodiment, the energy source 122 harvests or rectifies power from the IMD stimulation pulses and stores the same in order to power the electronic assembly 120. In yet another embodiment, the electronic assembly 120 is temporarily powered via an external magnetic field or RF energy.

The electronic assembly 120 may be integrated in one or multiple circuit boards that may be formed of biostable materials. In one embodiment, electronic assembly 120 is provided in two circuit boards, with each board being disposed at separate locations on the lead body 100. The first circuit board may house the electronics and circuitry associated with PWI module 124a and the second circuit board may house the electronics and circuitry associated with lead monitoring circuit 124b. An electrical pathway is provided between the two circuit boards for interconnection. In one embodiment, the electrical pathway is defined by conductors 224. In accordance with principles of the disclosure, each of the circuit boards making up electronic assembly 120 may be provided with similar or different functionality that may be employed in identifying lead-related conditions.

In one specific implementation of the disclosure the PWI module 124a receives analog signals from the electrodes associated with lead 18, although digital sensors and/or circuitry can be utilized in conjunction with the disclosure. In the depicted embodiment the received signals are a function of the electrical signals sensed at the monitoring site (e.g. RV 28) which can of course include myriad different locations on or about the heart and other muscles, circulatory system, nervous system, digestive system, skeleton, brain, and other body locations.

Figure 7:
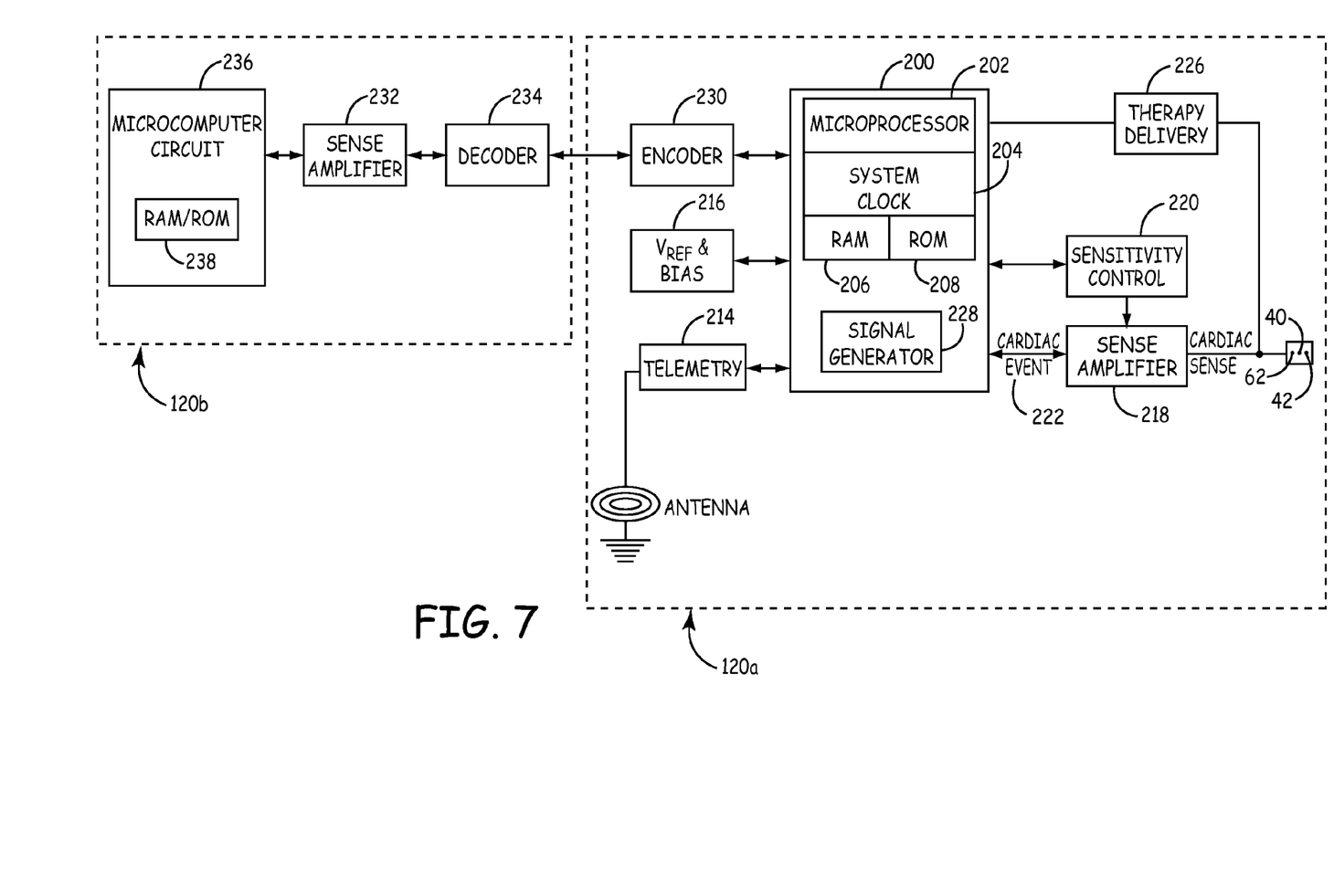
FIG. 7 is an exemplary schematic diagram illustrating components of an embodiment of an electrical assembly.

The PWI module 124a optionally includes a digital processor (FIG. 7). In operation, PWI module 124a obtains data about heart 12 via the electrodes 62, 40 and 42. This data is provided to the digital signal processor, which suitably analyzes the data and controls a signal generator (FIG. 7) to generate a minimal impact signal (MIS) as appropriate. An MIS (or event detection signal) is a signal that is less vulnerable to noise and other environmentally-induced distortions due to its signal properties. The environment may include the system hardware and other sources external to the system hardware. The MIS may comprise an analog waveform, discrete pulses or a pattern of bits. Also, the MIS may be encoded by, for example, defining one or more properties so as to facilitate the lead monitoring and sensing functions to distinguish between a physiological signal and a non-physiological signal. The predetermined set of properties will inherently minimize the impact of signal distortion due to bursts of unwanted signal frequencies and amplitudes related to occurrence of one or more lead-related conditions, including conditions that may be intermittent and irregular.

Examples of the MIS properties may include frequency (including compositions that may have multiple frequencies), width and duration (which may be in the microsecond range or shorter), amplitude compositions (that may be non-physiological) or rise and fall times. An example of an MIS signal may be a signal having a predefined series of pulses each with a unique set of MIS properties that may be the same or different with each pulse.

The MIS properties may facilitate an increase in the signal-to-noise ratio that may be encountered when propagating cardiac waveforms from cardiac tissue to sensing or lead monitoring circuits. It has been observed that signal-to-noise ratios are often low since the amplitude range of cardiac signals sensed by electrodes in the heart chambers is close to that of noise generated on the leads. The low signal-to-noise ratios give rise to aliasing or non-physiological waveforms masquerading as physiological waveforms. Therefore, MIS properties address the possibility of cardiac waveform aliasing due to lead-related conditions.

The MIS may be propagated from circuitry disposed along the lead, for example on the lead distal end, to represent a cardiac depolarization. A received signal at another location on or coupled to the lead, such as the proximal lead end or the implantable medical device MIS is then decoded and interpreted to determine whether it is the MIS. In other words, the decoding process includes determining whether the properties of the received signal match the MIS properties of the MIS signal that was generated within the lead. Lead monitoring circuits may determine that a lead-related condition exists in response to errors in decoding the received signal.

In accordance with aspects of this disclosure, the sensed cardiac signal may also be transmitted in conjunction with the MIS. In doing so, the MIS will validate the cardiac signal and/or provide a secondary indication of depolarization if the path that is transmitting the cardiac signal has a lead-related condition thereby supporting fault-tolerant architecture. As such, the MIS may also support detection of lead related conditions on a plurality of conductors through correlation of the signals on one or more conductors.

A plurality of minimal impact signals each having a unique set of one or more of the aforementioned MIS properties may be generated. For ease of description, the distinct MIS properties identifying each MIS will be referred to as an MIS signature. Thus in one example, a plurality of minimal impact signals each with a unique MIS signature may be pre-programmed in the processor for selection and generation by the signal generator. The MIS signature of each pulse may be varied based on the originating lead, for example, to differentiate identified cardiac events. For instance, a first MIS pulse signature may be defined for generation when a ventricular depolarization event is sensed by a first lead while a third pulse signature may be defined for an atrial depolarization event sensed by a second lead.

Optionally, the results of the heart data processing by processor (not shown) may be stored in memory (not shown). The PWI module 124a may alternatively transmit and receive signals to and from an external device (not shown) via communication such as radio frequency (RF) telemetry. In various embodiments, PWI module 124a activates an alarm (not shown) upon detection of an arrhythmic event. Alternatively or in addition to alarm activation, PWI module 124*a* may send a signal to the IMD that results in an adjustment of therapy (for example to be delivered on an alternative path) and/or coordinates the therapy delivery via electronic assembly 120, IMD 16 or another appropriate device. Therapies that may be applied in various embodiments may include drug delivery or electrical stimulation therapies such as cardiac pacing, resynchronization therapy, extra systolic stimulation, neurostimulation.

Figure 6:
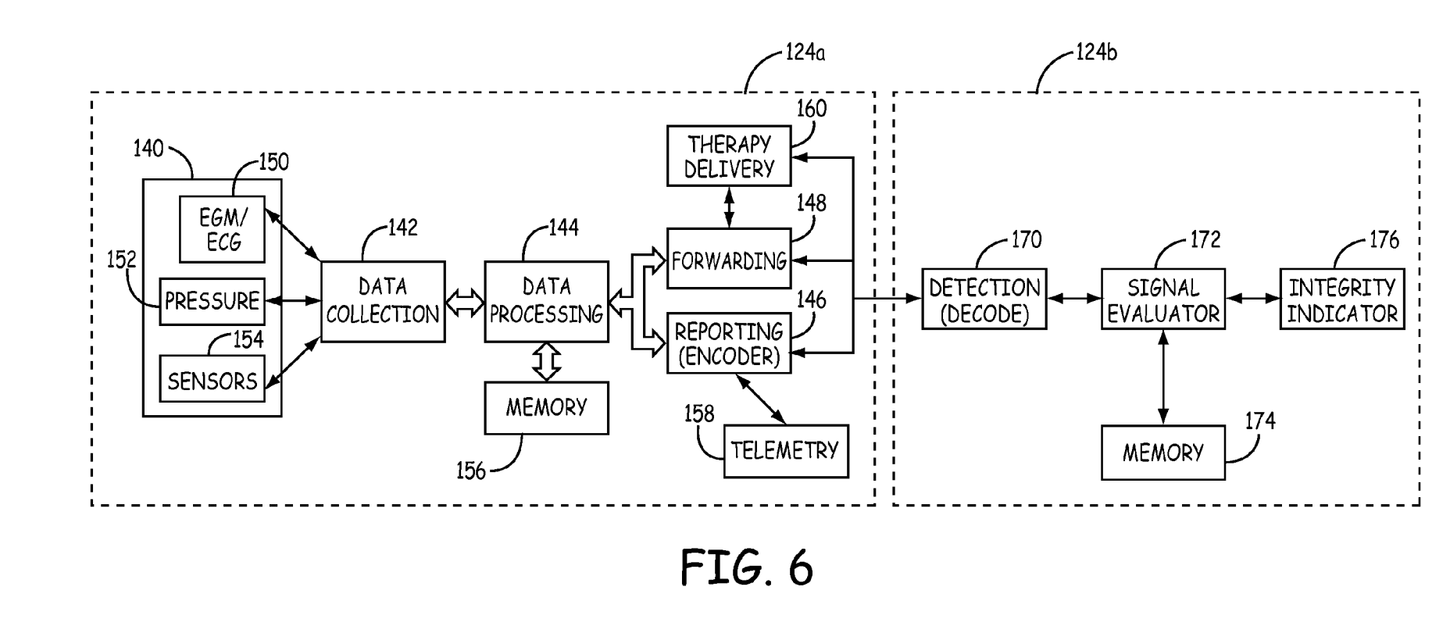
FIG. 6 is a block diagram illustrating physiological waveform interpretation and lead monitoring functions in accordance with embodiments of the present disclosure.

FIG. 6 is a block diagram summarizing the physiological waveform interpretation and lead monitoring functions in accordance with embodiments of the present disclosure. The physiological waveform interpretation and lead monitoring functions may be implemented in a system, such as electronic assembly 120 shown in FIG. 5. Alternatively, the physiological waveform interpretation and lead monitoring functions may be implemented in multiple modules within one or more of leads 18, 20, 22, IMD 16 and/or an external device (not shown) of the FIG. 2. One such exemplary implementation may comprise housing the physiological waveform interpretation function in a module within the lead 18 with the lead monitoring function being housed in the IMD 16. Alternative implementations may further split the physiological waveform interpretation function and/or the lead monitoring function in multiple modules contained within one or more leads 18, 20, 22, IMD 16 and/or an external device.

In general, the physiological waveform interpretation module includes one or more applications for acquiring physiological signal data from a patient. In one example, cardiac electrical signals are acquired by the physiological waveform interpretation module via a given lead from electrodes coupled to the lead with the signals being processed by the physiological waveform interpretation module to determine whether a cardiac event has occurred. Based on the processing results, the physiological waveform interpretation module subsequently generates an MIS that is transmitted to the lead monitoring module. In some embodiments, a plurality of MIS with each MIS corresponding to a specific detected event and each MIS having a distinct MIS signature may be available for selection. As such, an appropriate MIS signature is selected based on the detected cardiac event. Subsequent to generating the MIS, the physiological waveform interpretation module transmits the signal to the lead monitoring module.

In accordance with principles of the present disclosure, the lead monitoring module analyzes the signal received to decode or extract information such as the MIS properties from the signal. In doing so, the lead monitoring circuit will determine whether the received signal is indeed an MIS. For example, the signal will be confirmed to be an MIS if the signals properties are recognized to be MIS properties. MIS properties may be extracted and/or decoded in real-time by decoding circuits, by comparison circuits, and by signal processing circuitry.

MIS properties of a received signal may also be evaluated by comparing the signal properties to a pre-stored MIS set of properties. In exemplary implementations, the lead monitoring module may include a template of stored MIS properties and various signatures. A comparison of the template signals may then be performed to determine whether the received signal matches the stored templates, is consistent with an event, confirms occurrence of an event, and/or whether the received signal is corrupted. A simultaneous comparison or comparison to predetermined threshold levels may also be performed. The results of the comparison of the MIS signatures or MIS properties may then be transmitted to the IMD 16 for appropriate action. Additionally, the received MIS may be transmitted to the IMD 16 for determination of the appropriate therapy delivery. In another implementation, signal comparison may refer to comparison of the received signal to a specific set of diagnostic properties. A diagnostic property is any property contributing to the diagnostic analysis of a signal. Diagnostic property information may be stored in memory, in the signal, in an algorithm, in the signal monitoring hardware itself or any combination of the possibilities.

Referring to FIG. 6, the PWI module 124*a* includes a data collection unit 142 that receives data from a data source 140, a data processing unit 144, a reporting unit 146 and a forwarding unit 148. In the illustrative embodiment, data source 140 may include electrodes 150 for acquiring EGM/ECG data, a pressure sensor 152 and/or other sensors 154 for acquiring physiological signals useful in monitoring a cardiac condition such as an accelerometer or wall motion sensor, a blood flow sensor, a blood gas sensor such as an oxygen sensor, a pH sensor, or impedance sensors for monitoring respiration, lung wetness, or cardiac chamber volumes. The various data sources 140 may be provided alone or in combination with each other, and may vary from embodiment to embodiment. Some of the various units of the PWI module may be implemented with computer-executable instructions stored in memory and executing on a processor or in any other manner.

Data collection unit 142 receives data from each of the data sources 140—by polling each of the sources 140, by responding to interrupts or other signals generated by the sources 140, by receiving data at regular time intervals, or according to any other temporal scheme. Data may be received at data collection unit 142 in digital or analog format according to any protocol. If any of the data sources generate analog data, data collection unit 142 may translate the analog signals to digital equivalents using an analog-to-digital conversion scheme. Data collection unit 142 may also convert data from protocols used by data sources 140 to data formats acceptable to data processing unit 144, as appropriate.

Data processing unit 144 is any circuit, programming routine, application or other hardware/software application that is capable of processing data received from data collection unit 142. In various embodiments, data processing unit 144 is a software application executing on a processor (FIG. 7). Data processing unit 144 processes the data to identify physiological events such as the occurrence of a cardiac event. Upon identifying the physiological events, the signal processor may issue a control signal to reporting unit 146 to generate a signal.

Reporting unit 146 is any circuit or routine including a signal generator capable of producing or generating an MIS, such as a pulse. The reporting unit 146 may be controlled by the processor to generate a specific MIS with certain MIS properties or it may act independently to generate a default MIS based on a sensed event. The reporting unit 146 generates the specified MIS and transmits it to a lead monitoring module 124*b* through the appropriate conductors. In some embodiments, reporting unit 146 will include an encoder to encode the MIS with the predetermined set of MIS properties. Encoding the MIS signal will facilitate the reduction of aliasing and reduce susceptibility of the signal to noise and other unwanted behaviors associated with lead-related conditions.

In various embodiments, reporting unit 146 may include storing capability in memory 156 or generation of a wireless message for transmission by a telemetry circuit 158 that is in bidirectional telemetric communication with an external device. The external device receiving the wireless message may be a programmer/output device that advises the patient, a physician or other attendant of serious conditions (e.g., via a display or a visible or audible alarm). Information stored in memory 156 may be provided to the external device to aid in diagnosis or treatment of the patient. Alternatively, the external device may be an interface to a communications network such that the PWI module 124a is able to transfer data to an expert patient management center or automatically notify medical personnel if an extreme episode occurs.

Forwarding unit 148 comprises any circuit, software application or other component that functions as a signal repeater that will generally re-transmit the data collected by data collection unit 142 to the lead monitoring module. In some embodiments, forwarding unit 148 may alternatively or additionally interact with a therapy delivery unit 160 to deliver pacing, extra systolic stimulation, cardioversion, defibrillation and/or any other therapy as desired. Accordingly, commands may be issued externally or by the signal processor (FIG. 7) directing the provision of therapy in various embodiments. As such, if the existing conditions prevent the provision of therapy from IMD 16, therapy delivery application may provide substitute therapy.

With the above in mind, it should be understood that the functionality of the lead monitoring module 124b comprises detection of the transmitted MIS and determination of the integrity of the received signal. As such, a detection unit 170 senses for transmitted signals on the coupling conductor. The signal received by detection unit 170 is evaluated by signal evaluation unit 172 to determine whether the received signal is indicative of an integrity issue of the coupling conductor(s). In embodiments where the reporting unit 146 includes an encoder, a decoder may be included in the detection unit 170 for deciphering the received signal. In such embodiments, successfully deciphering the received signal may be a sufficient indicator that there are no detected lead-related conditions because the MIS was transmitted successfully. In another example, the signal evaluation unit 172 may implement signal comparison techniques whereby one or more templates stored in memory 174 are compared with the received signal to determine whether there is a match. In another example, the received signal may be processed by the signal evaluation unit 172 to determine whether one or more characteristics are within predetermined values. The range of acceptable deviation may be stored in memory 174 for retrieval by signal evaluation unit 172 during the signal evaluation.

The results of the evaluation of the MIS are provided to the IMD 16 for determination of whether further action is required. In an embodiment, a lead component integrity indicator unit 176 is provided for communicating with IMD 16. In an example, the results of the processing of the MIS may be transmitted to an external device for further processing to determine whether a lead-related condition is present and if so, the action to be taken. A notification may also be communicated to alert the patient and/or clinician of the determination of that a lead-related condition has been detected. Suitable communication schemes between unit 176 and IMD 16 and/or the external device may include any known schemes such as telemetry, fiber optic, and hardwired medium.

IMD 16 may take one or more actions in response to the detection of a lead-related condition. For example, sensing and/or therapy delivery may be reconfigured to avoid use of a conductor pathway that has been identified as having a lead-related condition. Additionally or alternatively, sensing and/or therapy delivery parameters may be reconfigured to permit continued use of a conductor pathway having a lead-related condition. As one example, different combinations of electrodes may be selected to deliver therapy to patient 14. As another example, the blanking period of one or more sensing channels may be extended to accommodate the lead-related condition. In one more example, a sensing threshold may be increased—e.g., a threshold used to detect cardiac events such as depolarizations—following delivery of a therapeutic electrical signal, e.g., an antitachycardia pacing pulse. Extending a blanking period and/or increasing a threshold value may help prevent inappropriate detection of arrhythmias and/or other cardiac events.

The functional reconfiguration on detection of a lead-related condition may be achieved automatically or by reprogramming. The option to reprogram functionality and to reconfigure provides an alternative to lead extraction while maintaining pacing and sensing functionality even after impairment of a particular conductor pathway. Automatic reprogramming and reconfiguration ensures that therapy will continue to be delivered to the patient even after impairment of a lead's conductive pathway.

FIG. 7 is an example schematic diagram illustrating certain components of an electrical assembly 120. For ease of description, the various components of the electronic assembly have been illustrated as being implemented in a single schematic. However, functional portions of the components and modules may alternatively be implemented in separate schematics as previously described. For example, while the PWI module 124a illustrated in FIG. 6 will typically be implemented in a lead in some embodiments, the lead monitoring functionality 124b may be included either within the lead, or within IMD 16 or even within an external device.

As discussed in conjunction with FIG. 1, lead 18 may include one or more electrodes 62, 40, 42. Electronic assembly 120a contains the analog circuits for interface to the heart 12 as well as circuits for generating signals for determination of lead-related conditions. It will be understood that each of the electrical components represented in FIG. 7 may be powered by an appropriate power source 122 as previously described.

Microcomputer circuit 200 comprises a microprocessor 202 having an internal system clock circuit 204, and on-board RAM 206 and ROM 208. Microcomputer circuit 200 controls the timing of the sensing functions and other device functions in accordance with a programmed operating mode.

To facilitate communication with the external device, an antenna 212 may be connected through an RF telemetry circuit 214 for purposes of telemetry in accordance with one embodiment of the disclosure. It is contemplated that telemetry circuit 214 may also be coupled directly to microcomputer circuit 200. A $V_{REF}$ and Bias circuit 216 generates stable voltage reference and bias currents for the analog circuits of microcomputer circuit 200.

Microcomputer circuit 200 is coupled to sensing circuitry including a sense amplifier circuit 218 and a sensitivity control circuit 220. In particular, microcomputer circuit 200 receives a cardiac-EVENT signal on line 222. Sense amplifier circuit 218 is electrically coupled to the electrodes on lead 18 via conductors 224a, in order to receive the cardiac signals from heart 12. The cardiac-EVENT signal may either be an atrial or ventricular event depending on the chamber in which the electrodes are implanted.

Sense amplifier circuit 218 will assert the cardiac-EVENT signal on line 222 when a cardiac event (e.g., a paced or intrinsic atrial event) is detected. Sense amplifier circuit 218 includes one or more sense amplifiers. Sensitivity control 220 is provided to adjust the gain of sense amplifier circuit 218 in accordance with programmed sensitivity settings. The cardiac-EVENT signal is processed by microcomputer circuit 200 in accordance with known processing techniques to determine whether the signal is indicative of a cardiac event.

After determining that the cardiac-EVENT signal is indicative of a cardiac event, the microprocessor will control a signal generator 208 to generate a PWI signal. The control data will include the signature of the PWI signal to be generated, with the signature corresponding to the appropriate sensed cardiac event. The generated MIS is subsequently placed on the distal end of conductor(s) 224b for transmission. In some embodiments, the generated MIS may further be encoded by an encoder 230 prior to transmission.

A second sense amplifier 232 is coupled to the proximal end of conductor(s) 224b for sensing the MIS transmitted by microcomputer circuit 200. In embodiments including encoding of the MIS, a decoder 234 is coupled to sense amplifier 232 to decode a received signal. A second microcomputer circuit 236 may then be coupled to the sense amplifier 232 to receive and process the received signal as discussed in conjunction with the lead monitoring functions. Microcomputer circuit 236 may further include a RAM/ROM unit 238 for storage of the results of the processing and/or the received signal.

In some alternative embodiments, the results of the processing by microcomputer circuit 236 may be utilized as previously discussed to determine whether a therapy should be delivered. In such implementations, a therapy delivery circuit 226 may additionally be coupled to microcomputer circuit 200. Microcomputer circuit 200 provides signals to therapy delivery circuit 226 for delivery of therapy to heart 12. In particular, various capacitors (not shown) for storage of energy for therapy delivery may be supplied with the energy by energy source 122 and discharged across heart 12. Therapy delivery circuit 226 is also coupled to one or more of the conductors 224a in lead 18 for delivering electrical stimulation pulses via the electrodes on lead 18. Therapy delivery circuit 226 selects which electrodes and corresponding polarities are used for delivering electrical stimulation pulses.

As will be appreciated by those of ordinary skill in the art, the application of a therapy to one chamber of the heart is a multiple-step process. The process is initiated by microcomputer circuit 200 in response to a predetermined set of conditions. For example, microcomputer circuit 200 may function to initiate delivery of a ventricular pacing pulse only when a predetermined time interval elapses following a paced or natural atrial event with no natural ventricular event being detected during that time period. It is believed that the details of such therapy delivery algorithm, i.e., the various conditions, time intervals, algorithms, and the like that define the therapy delivery functions are not critical to an understanding of the present disclosure, and will not be described herein in substantial detail. For the purposes of the present disclosure, it is sufficient to state that microcomputer circuit 200 implements an algorithm and at various times may take steps to initiate delivery of therapy.

Also, electronic assembly 120a will include decoupling circuitry for temporarily decoupling various components such as sense amplifier circuit 218 from the electrode-coupling conductors when stimulating pulses are being delivered from therapy delivery circuit 84. For the sake of clarity, such decoupling circuitry is not depicted in FIG. 7.

Figure 8:
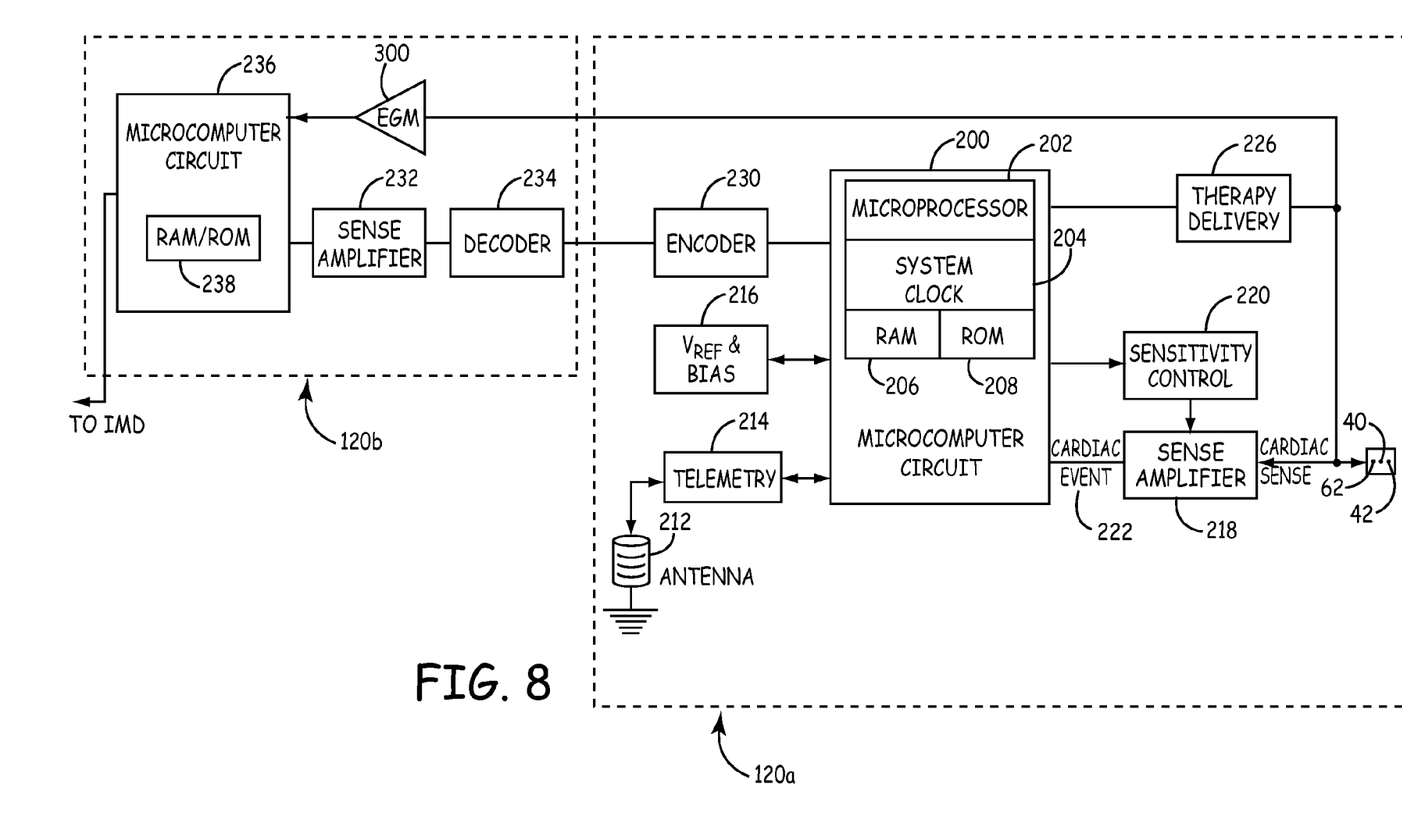
FIG. 8 is an exemplary schematic diagram illustrating certain components of an alternative embodiment of an electrical assembly.

FIG. 8 illustrates a schematic diagram illustrating an alternative embodiment of an electronic assembly for the lead of FIG. 5. The elements of electronic assembly 120b corresponding to those of electronic assembly 120a are numbered with identical reference designators. The reader is referred to the preceding description of FIG. 7 for a full discussion pertaining to those components.

An EGM (electrocardiogram) amplifier 300 is coupled to a conductor 224c to receive the cardiac-SENSE signal from heart 12. Again, cardiac-SENSE signal may either be an atrial or ventricular signal depending on which chamber the lead is implanted into. A representation of the analog electrogram signals of the patient's electrical heart activity developed by EGM amplifier 300 may be stored in RAM/ROM 238 for subsequent retrieval and transmission by uplink telemetry via an external programmer (not shown) and/or directly transmitted to the IMD 16 on those occasions when the implanted device is being interrogated by the external programmer.

The embodiment of FIG. 8 may be usefully employed to provide an additional exemplary technique for identifying the presence of a lead-related condition. In this implementation, microcomputer 236 compares the number of incoming MIS on conductor 224b against the number of cardiac-SENSE signals detected by EGM amplifier 300. Multiple conductors on one lead may typically, although not necessarily, be utilized to transmit the cardiac-SENSE signals and the MIS. Therefore, for each event (atrial or ventricular) detected by EGM amplifier 300, a corresponding MIS should be received. A mismatch between the number of events detected by EGM amplifier 300 and the number of received MIS will trigger a determination of a lead-related condition.

Functionality associated with one or more modules or units to support the various operations and functions described in this disclosure may be performed by separate hardware, software or firmware components, or integrated within common or separate hardware or software components in one or more devices. In addition, any of the described units, applications, modules or components may be implemented together or separately as discrete but interoperable logic devices. As such, the various functions of each module may in practice be combined, distributed or otherwise differently-organized in any fashion across the implantable systems of FIGS. 1-3. Thus, depiction of different features as modules or units is intended to highlight different functional aspects and does not necessarily imply that such modules or units must be realized by separate hardware or software components.

The techniques described in this disclosure, including those attributed to the implantable leads, IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated, analog, or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

Various examples for detecting lead-related conditions have been described. It should be appreciated that the exemplary embodiments are only examples, and are not intended to limit the scope, applicability, or configuration of the disclosure in any way. Rather, the foregoing detailed description will provide those skilled in the art with a convenient road map for implementing the exemplary embodiments. It should also be understood that various changes can be made in the function and arrangement of elements without departing from the scope of the disclosure as set forth in the appended claims and the legal equivalents thereof.

What is claimed is:

1. An implantable medical system, comprising:
  an electrode;
  a medical electrical lead coupled to the electrode, including
    a physiological waveform interpreter (PWI) module having:
      a data collection unit coupled to the electrode and configured to receive an electrical signal of a physiological signal sensed by the electrode; and
      a reporting unit coupled to the data collection unit configured to generate a predetermined minimal impact signal that is indicative of the physiological signal in response to the sensed signal, the minimal impact signal having a different electrical property from the sensed signal; and
  a medical device coupled to the lead including a lead monitoring circuit for receiving the minimal impact signal and processing the signal to determine whether a lead-related condition associated with the lead is present.

2. The implantable medical system of claim 1, wherein the PWI module comprises:
  a sensing module for receiving the sensed electrical signals;
  a processor coupled to the sensing module for processing the sensed electrical signals; and
  a signal generator for generating the minimal impact signal.

3. The implantable medical system of claim 1, wherein the PWI module includes an encoder configured to encode the minimal impact signal.

4. The implantable medical system of claim 3, wherein the lead monitoring circuit comprises a decoder configured to decode the minimal impact signal.

5. The implantable medical system of claim 4, wherein the lead-related condition is determined to be present in response to a mismatch between the received decoded minimal impact signal and the generated minimal impact signal.

6. The implantable medical system of claim 1, wherein PWI module modulates a signature of the minimal impact signal in response to predetermined criteria.

7. The implantable medical system of claim 6, wherein the predetermined criteria includes the chamber in which the electrical signal is sensed.

8. The implantable medical system of claim 6, wherein the predetermined criteria includes the sensing of an intrinsic cardiac event.

9. The implantable medical system of claim 1, further comprising a signal evaluation unit configured to compare one or more properties of the received signal to a stored set of minimal impact signal properties to determine whether the lead-related condition is present.

10. The implantable medical system of claim 1, wherein the lead includes a conductor encapsulated by an insulative member and the lead-related condition comprises a defect of at least one of the conductor and the insulative member.

11. The implantable medical system of claim 1, wherein the minimal impact signal comprises predefined signal characteristics that are selected such that the minimal impact signal has a higher signal-to-noise ratio relative to a signal-to-noise ratio of the sensed electrical signal.

12. An implantable medical electrical lead, comprising:
  a lead body;
  an electrical conductor disposed within the lead;
  a physiological waveform interpreter (PWI) module coupled to the electrical conductor, the PWI module including:
    a data source for monitoring electrical signals indicative of a physiological event; and
    a reporting unit configured to generate a minimal impact signal that is indicative of the physiological event in response to sensing a physiological event, the minimal impact signal having at least one electrical property that is different from the monitored electrical signals.

13. The implantable medical electrical lead of claim 12, wherein the monitored electrical signal is indicative of an intrinsic cardiac event.

14. The implantable medical electrical lead of claim 12, wherein the monitored electrical signal is indicative of a delivered pacing pulse having exceeded a capture threshold of cardiac tissue.

15. The implantable medical electrical lead of claim 12, further comprising means for telemetering a signal in response to sensing the physiological event.

16. The implantable medical electrical lead of claim 12, wherein the PWI module includes an encoder configured to encode the minimal impact signal.

17. The implantable medical electrical lead of claim 12, further comprising lead monitoring circuit for receiving the minimal impact signal and processing the signal to determine whether a lead-related condition is present.

18. The implantable medical electrical lead of claim 13, wherein the lead monitoring circuit is disposed on a proximal end of the lead body and the PWI module is disposed on a distal end of the lead body.

* * * * *

UNITED STATES PATENT AND TRADEMARK OFFICE
CERTIFICATE OF CORRECTION

| | | |
|---|---|---|
| PATENT NO. | : 8,855,765 B2 | Page 1 of 1 |
| APPLICATION NO. | : 13/156632 | |
| DATED | : October 7, 2014 | |
| INVENTOR(S) | : Thomas H. Spear et al. | |

It is certified that error appears in the above-identified patent and that said Letters Patent is hereby corrected as shown below:

In the Claims

Column 18, lines 48-49, delete "electrical lead of claim 13, wherein the lead" and insert in place thereof --"electrical lead of claim 17, wherein the lead"--

Signed and Sealed this
Twenty-ninth Day of September, 2015

Michelle K. Lee
*Director of the United States Patent and Trademark Office*